United States Patent [19]

Mouzin et al.

[11] Patent Number: 4,539,413
[45] Date of Patent: Sep. 3, 1985

[54] PREPARATION OF 3-AMINO-1-[(1,4-BENZODIOXAN)-2-YL-METHOXY]-2-PROPANOLS

[75] Inventors: Gilbert Mouzin; Henri Cousse, both of Castres; Pol Vilain, Labruguiere, all of France

[73] Assignee: Pierre Fabre S.A., Paris, France

[21] Appl. No.: 455,125

[22] Filed: Jan. 3, 1983

Related U.S. Application Data

[62] Division of Ser. No. 250,407, Apr. 2, 1981, Pat. No. 4,456,614.

[30] Foreign Application Priority Data

Apr. 4, 1980 [FR] France ................. 80 07719

[51] Int. Cl.³ ........................................ C07D 319/14
[52] U.S. Cl. .................................... 549/366
[58] Field of Search ................. 549/366, 362, 378

[56] References Cited

U.S. PATENT DOCUMENTS

| 4,187,313 | 2/1980 | Gschwend et al. | 549/366 |
| 4,221,807 | 9/1980 | Smith | 549/362 |
| 4,261,907 | 4/1981 | Gschwend et al. | 549/362 |

FOREIGN PATENT DOCUMENTS

| 0037778 | 10/1981 | European Pat. Off. | 549/366 |
| 0077081 | 7/1978 | Japan | 549/366 |

OTHER PUBLICATIONS

Augstein et al., Journ. Med. Chem., 8(4), pp. 446–456, (1965).

Primary Examiner—Ethel G. Love
Attorney, Agent, or Firm—Gordon W. Hueschen

[57] ABSTRACT

The present invention concerns a novel process for the production of new chemical compounds of the general formula:

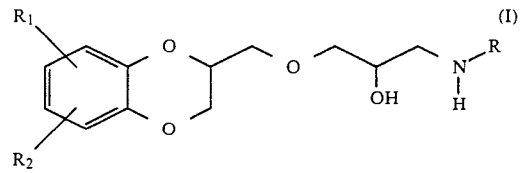

in which:

$R_1$ and $R_2$ may be identical or different and represent a hydrogen or halogen atom or else a lower alkyl, lower alkoxy, nitro or acetyl group and R represents a lower alkyl or lower aralkyl group, such as benzyl.

These compounds are useful in therapy for the treatment of hypertension and cardiac arrhythmia.

The novel process involves reaction of a 2-hydroxymethyl-1,4-benzodioxan with epichlorohydrin to produce an intermediate glycidyl ether, which is then reacted with a primary amine to produce the final 3-amino-1-[(1,4-benzodioxan)-2-yl-methoxy]-2-propanol or an acid addition salt thereof.

11 Claims, No Drawings

PREPARATION OF 3-AMINO-1-[(1,4-BENZODIOXAN)-2-YL-METHOXY]-2-PROPANOLS

This is a division of application Ser. No. 250,407, filed Apr. 2, 1981, now U.S. Pat. No. 4,456,614.

The present invention, developed at the PIERRE FABRE Research Center, has as its object new chemical compounds, their method of preparation and their use in therapy, particularly for the treatment of hypertension and arrythmias of various origins.

The invention also relates to pharmaceutical compositions containing these active principles.

The present invention refers to new chemical compounds having general formula I:

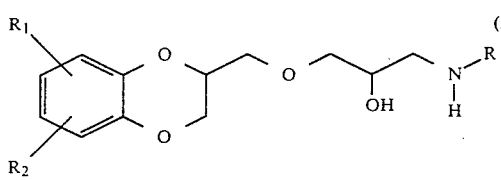

in which:
R₁ and R₂ may be identical or different and represent a hydrogen or halogen atom or else a lower alkyl, lower alkoxy, nitro or acetyl group and
R represents a lower alkyl or a lower aralkyl group, such as benzyl, as well as their salts with therapeutically acceptable inorganic or organic acids.

Acids capable of leading to therapeutically acceptable salts of compounds of formula I are, for instance, hydrochloric acid, sulfuric acid, phosphoric acid, succinic acid, oxalic acid, tartaric acid, maleic acid and fumaric acid.

By lower alkyl radical there will be understood essentially linear or branched alkyl radicals containing from 1 to 8 carbon atoms and preferably 1 to 4 carbon atoms.

In accordance with the present invention, the new compounds of formula I can be prepared by a process which comprises the following two reaction steps:

1st STEP

Preparation of the glycidyl ether of 2-hydroxymethyl benzodioxan

By condensation of epichlorhydrin with a 2-hydroxymethyl benzodioxan derivative of formula II in the presence of a base such as caustic soda and of a catalyst of quaternary ammonium type having the formula

there is obtained the glycidyl ether of formula III

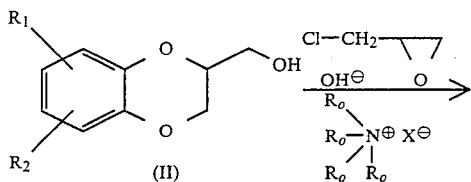

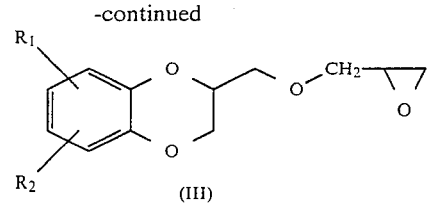

in which formulas the radicals R₁ and R₂ have the same meanings as those given previously with respect to formula I, R$_o$ represents a lower alkyl radical and X$^\ominus$ the anion of an acid, for instance HSO$_3^\ominus$ or Hal$^\ominus$.

The 2-hydroxymethyl benzodioxan derivatives of formula II which are used as synthesis intermediates can be prepared, for instance, by the method of J. AUGSTEIN et al.—*J. Med. Chem.* 8, 446 (1965).

2nd STEP

By opening the intermediate epoxide of formula III by means of a primary amine of formula IV the derivatives of formula I are obtained:

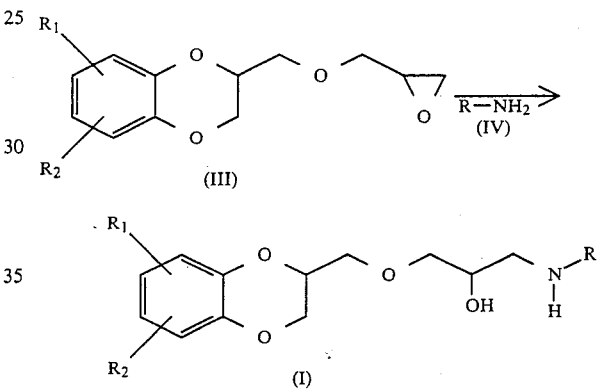

in which formulas the radicals R, R₁ and R₂ have the same meaning as given previously with respect to formula I.

The following chemical compounds and their manner of preparation are cited by way of illustration and not of limitation:

EXAMPLE 1

Preparation of 3-tertiobutylamino-1-[(1,4-benzodioxan)-2-yl methoxy]-2-propanol maleate (a) Preparation of (1,4-benzodioxan)-2-yl methyl glycidyl ether To a heterogenous mixture of 100 ml of epichlorhydrin, 100 ml of 50% caustic soda and 1.4 g of tetrabutylammonium hydrogen sulfate there are added, with good agitation, 16.6 g (0.1 mol) of 2-hydroxymethyl-1,4-benzodioxan.

The reaction is set aside for two hours at room temperature whereupon 100 ml of water and 200 ml of ethyl acetate are added. After settling and washing of the organic phase with water, a bicarbonate solution and then water saturated with sodium, it is dried over sodium sulfate.

After filtration and evaporation of the solvent the glycidyl ether is obtained in quantitative yield.

(b) Preparation of
3-tertiobutylamino-1-[1,4-benzodioxan)-2-yl
methoxy]-2-propanol maleate To an iced solution of 21 ml (14.6 g–0.2 mol) of tertiobutylamine in 200 ml of methanol, there are added 50 mmols (14.25 g) of (1,4-benzodioxan)-2-yl methyl glycidyl ether.

After stirring for three hours at room temperature, the reaction mixture is brought to reflux for one hour. It is left overnight at room temperature and then evaporated to dryness. The residual oil is taken up with ethyl ether, washed three times with water and then dried over sodium sulfate. The resultant solution is filtered and treated with 6 g of maleic acid dissolved in 200 ml of ethyl ether. It is iced and filtered; the crude crystals obtained are recrystallized from a mixture of ethyl acetate and isopropyl ether.

The product of the formula

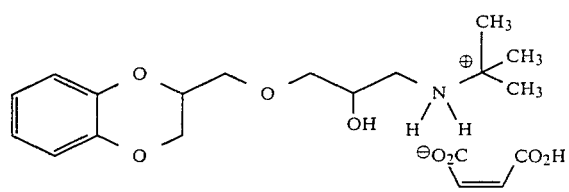

is recovered with a yield of 75%.
Empirical formula: $C_{20}H_{29}NO_8$
Molecular weight: 411.4
Crystals: White
Melting point: 90° C.
Plate chromatography:
Solvent: chloroform-methanol-ammonia 80/18/2
Support: Silica gel 60 F 254 Merck
Development: UV and iodine
Rf: 0.5
Solubility: 10% soluble in water.

EXAMPLE 2

Preparation of
3-tertiobutylamino-1-[(6-methyl-1,4-benzodioxan)-2-yl methoxy]-2-propanol hydrochloride In a manner similar to that described in Example 1 but using 2-hydroxymethyl-6-methyl-1,4-benzodioxan, tertiobutylamine and hydrochloric acid as salinifying agent, there is obtained the product of the formula:

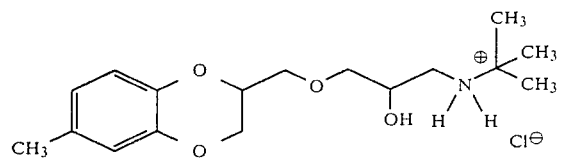

EXAMPLE 3

Preparation of
3-tertiobutylamino-1-[(5-methyl-1,4-benzodioxan)-2-yl methoxy]-2-propanol hydrochloride In a manner similar to the preceding example but using 2-hydroxymethyl-5-methyl-1,4-benzodioxan, there is obtained the product of the formula:

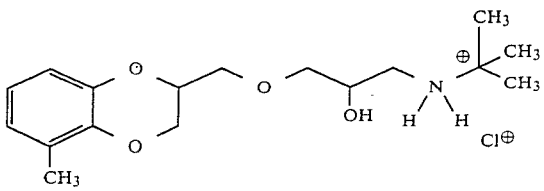

EXAMPLE 4

Preparation of
3-tertiobutylamino-1-[(7-methyl-1,4-benzodioxan)-2-yl-methoxy]-2-propanol hydrochloride In a manner similar to that described in Example 1 but using 2-hydroxymethyl-7-methyl-1,4-benzodioxan, tertiobutylamine and hydrochloric acid as salinifying agent, there is obtained the product of the formula:

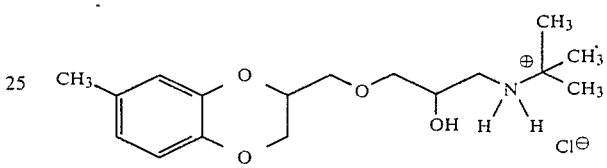

EXAMPLE 5

Preparation of
3-tertiobutylamino-1-[(8-methyl-1,4-benzodioxan)-2-yl-methoxy]-2-propanol hydrochloride In a manner similar to that described in Example 1 but using 2-hydroxymethyl-8-methyl-1,4-benzodioxan, tertiobutylamine and hydrochloric acid as salinifying agent, there is obtained the product of the formula:

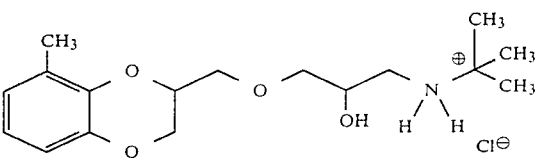

EXAMPLE 6

Preparation of
3-isopropylamino-1-[(5-chloro-1,4-benzodioxan)-2-yl-methoxy]-2-propanol fumarate In a manner similar to that described in Example 1 but using 2-hydroxymethyl-5-chloro-1,4-benzodioxan, isopropylamine and fumaric acid as salinifying agent, there is obtained the product of the formula:

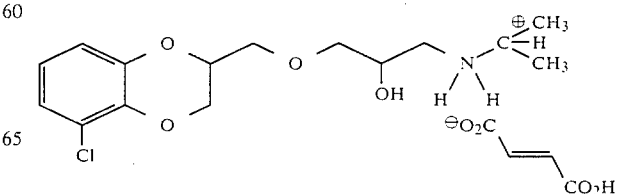

EXAMPLE 7

Preparation of
3-isopropylamino-1-[(7-chloro-1,4-benzodioxan)-2-yl-methoxy]-2-propanol fumarate In a manner similar to that described in Example 1 but using 2-hydroxymethyl-7-chloro-1,4-benzodioxan, isopropyl amine and fumaric acid as salinifying agent, there is obtained the product of the formula:

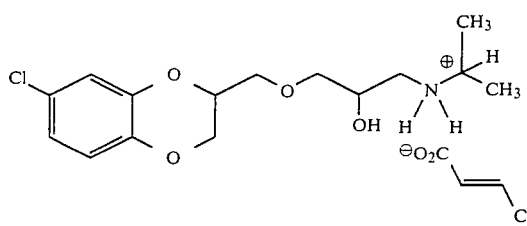

EXAMPLE 8

Preparation of
isopropyl-3-amino-1-[(7-nitro-1,4-benzodioxan)-2-yl-methoxy]-2-propanol hydrochloride In a manner similar to that described in Example 1 but using 2-hydroxymethyl-7-nitro-1,4-benzodioxan, isopropyl amine and hydrochloric acid as salinifying agent, there is obtained the product of the formula:

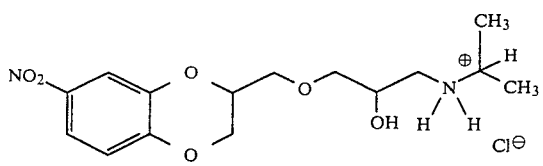

EXAMPLE 9

Preparation of
3-tertiobutylamino-1-[(7-methoxy-1,4-benzodioxan)-2-yl-methoxy]-2-propanol hydrochloride In a manner similar to that described in Example 1 but using 2-hydroxymethyl-7-methoxy-1,4-benzodioxan, tertiobutylamine and hydrochloric acid as salinifying agent, there is obtained the product of the formula:

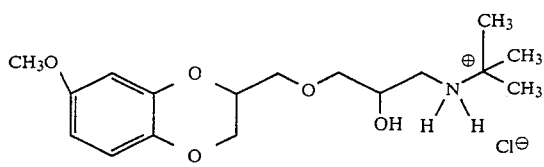

EXAMPLE 10

Preparation of
3-tertiobutylamino-1-[(6-acetyl-1,4-benzodioxan)-2-yl-methoxy]-2-propanol maleate In a manner similar to Example 1 but using 2-hydroxymethyl-6-acetyl-1,4-benzodioxan, tertiobutyl amine and maleic acid as salinifying agent, there is obtained the product of the formula:

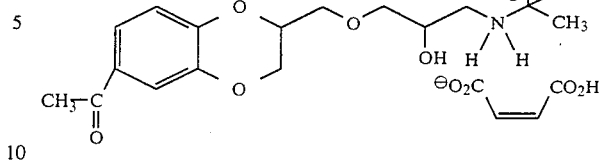

EXAMPLE 11

Preparation of
3-tertiobutylamino-1-[(5,7-dimethyl-1,4-benzodioxan)-2-yl-methoxy]-2-propanol hydrochloride In a manner similar to that described in Example 1 but using 2-hydroxymethyl-5,7-dimethyl-1,4-benzodioxan, tertiobutylamine and hydrochloric acid as salinifying agent, there is obtained the product of the formula:

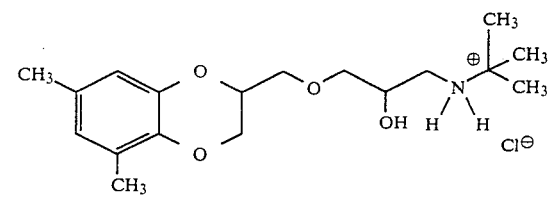

EXAMPLE 12

Preparation of
3-tertiobutylamino-1-[(6,7-dichloro-1,4-benzodioxan)-2-yl-methoxy]-2-propanol hydrochloride In a manner similar to that described in Example 1 but using 2-hydroxymethyl-6,7-dichloro-1,4-benzodioxan, tertiobutylamine and hydrochloric acid as salinifying agent, there is obtained the product of the formula:

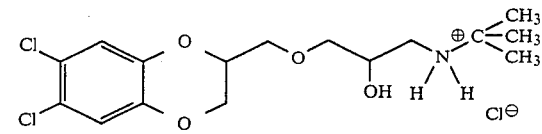

EXAMPLE 13

Preparation of
3-benzylamino-1-[(1,4-benzodioxan)-2-yl-1-methoxy]-2-propanol maleate In a manner similar to that described in Example 1 but using benzylamine, there is obtained the product product of the formula:

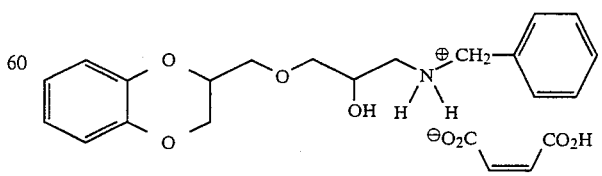

The new compounds of formula I of the present invention, which have good anti-hypertension and anti-arrhythmic pharmacological properties, can also be used in therapy, in particular for the treatment of hypertension and arrythmias of various origin.

It has been possible to establish these pharmacological properties by means of the following experiments.

EXPERIMENTS

(A) Toxicology

The chemical compounds described above were subjected to toxicity tests. The study of the toxicity was carried out on the conventional mouse weighing from 20 to 22 g.

The substances were administered intravenously and orally. The $LD_{50}$ was calculated in accordance with the method of G. KARBER, *Arch. Exptl. Pathol. Pharmacol.*, 162, 1931, 480.

The $LD_{50}$ values by intravenous injection are between 30 and 100 mg/kg. By oral administration the $LD_{50}$ values are between 600 and 900 mg/kg.

(B) Pharmacological Study

The pharmacological experiments to which the chemical compounds forming the object of the invention were subjected made it possible to show the following pharmacological properties:
anti-arrhythmic
beta-blocking
anti-hypertensive.

In order to illustrate these tests, we describe below the results obtained with the compound of Example 1, namely: 3-tertiobutylamino-(1,4-benzodioxan)-2-yl-1-methoxy-2-propanol maleate.

(1) Determination of anti-arrhythmic properties (a) Action with respect to ventricular tachycardia of digitalic origin (LUCHESI and HARDMAN—*J. Pharmacol. exp. Ther.*, 1961, No. 132, pages 372 to 81).

Method: Creation of a stable ventricular tachycardia in ten dogs (anesthetized) by successive intravenous injections of ouabain.

Results: The compound 3-tertiobutylamino-1-[(1,4-benzodioxan)-2-yl-methoxy]-2-propanol maleate, in doses of 2 and 5 mg/kg, opposes ectopic rhythm in all the animals.

The period of activity is more than 30 minutes in 80% of the cases.

(b) Influence on an auricular tachycardia produced by aconitine.

Method: (D. SCHERF—*Proc. Soc. exp. Biol.*, 1947, 64, 233). A tachycardia is caused in dogs by intramural injection of aconitine in the right atrium near the sinusoidal node.

The rhythm is increased in proportions of 80 to 100%. The auriculo-ventricular tracks show normal permeability, the ventricles are driven at the same frequency.

Results: The compound 3-tertiobutylamino-1-[(-1,4-maleate, in a dose of 5 mg/kg in vitro, reduces auricular tachycardia substantially and lastingly (% reduction of 60%—progressive return to the pathological rhythm, but the effect of the product persists for 30 minutes after injection).

(c) Effect on the frequency of spontaneous flutterings of the isolated atrium.

Method: Rabbit right atrium in survival in a Ringer-Locke's solution. The substances to be studied are introduced into the tank (at the rate of 0.5 and 1 mg per 100 ml) and remain in contact with the myocardial tissue for 24 minutes.

Results: The compound 3-tertiobutylamino-1-[(1,4-benzodioxan)-2-yl-methoxy]-2-propanol maleate has definitely a less negative chronotropic effect than dihydroquinidine.

Percentage of reduction of the frequency after 24 minutes:
Dihydroquinidine (1 mg): −35%
Compound 3-tertiobutylamino-1-[(1,4-benzodioxan)-2-yl-methoxy]-2-propanol maleate (1 mg): −16%

(d) Activity on the electrosystolic entrainment of the isolated rabbit atrium (G. S. DAWES—*Pharmacol. Rev.*, 4, 43–84, 1952).

Method: Rabbit right atrium in a Ringer-Locke's solution.

After determination of the threshold voltage for the entrainment of the muscle, the latter is subjected to frequencies which increase in successive steps until obtaining a maximum frequency for which the tissue is incapable of responding to the stimuli.

The product is added to the bath. Three electric entrainments are effected in the following 25 minutes. The experiment is then continued for one hour after the rinsing of the tank.

Results: The compound 3-tertiobutylamino-1-[(1,4-benzodioxan)-2-yl-methoxy]-2-propanol maleate extends the functional refractory period of the isolated atrium in the same way as dihydroquinidine.

Percentage decrease of threshold:
Dihydroquinidine (0.5 mg): 45%
3-tertiobutylamino-1-[(1,4-benzodioxan)-2-yl-methoxy]-2-propanol maleate (0.5 mg): 51%

(2) Search for an inhibitory property of the adrenergic receptors (O. DUNLOP, P. SHANKS, *Brit J. Pharmacol.*, 1968, 32, pages 201–218).

Method: Isoprenaline tachycardia in dogs. Simultaneous recording of the heart rate and of the arterial pressure.

Results: The compound 3-tertiobutylamino-1-[(1,4-benzodioxan)-2-yl-methoxy]-2-propanol maleate significantly reduces the isoprenaline tachycardia starting with a dose of 1 mg/kg intravenously.

At 5 mg/kg, the beta-blocking effect is substantial and cardioselectivity is noted.

(3) Systemic effects in dogs

Doses used: 1, 2 and 5 mg/kg
Parameters noted:
  arterial pressure
  heart rate
  respiratory rate
  left intraventricular pressure
  contractability index
  flows:
    coronary
    renal
    vertebral
    femoral
    carotidian The compound 3-tertiobutylamino-1-[(1,4-benzodioxan)-2-yl-methoxy]-2-propanol maleate has little impact on the cardiovascular system. It nevertheless decreases the force of cardiac contraction and the peripheral resistances, thus providing a group of properties adapted to combat hypertension.

(4) Effect on the central nervous system

Potentialization of the barbiturate and chloralhydrate anesthesia in mice.
Dose: 100 mg/kg
Results: nothing to report
Anticonvulsant property (G. CHEN and R. PORTMAN, A.M.A. Arch. Neurol. Psychiat., 68, 498, 1952).

The compound of 3-tertiobutylamino-1-[(1,4-benzodioxan)-2-yl-methoxy]-2-propanol maleate does not protect mice from toxicity of pentetrazole administered subcutaneously (compound of 3-tertiobutylamino-1-[(1,4-benzodioxan)-2-yl-methoxy]-2-propanol maleate—orally—100 mg/kg).

Anti-depressant properties (W. J. LANG and S. GORSHORN Arch. Int. Pharmacodyn., 142, 457, 1963).

No potentialization of toxicity to yohimbine in mice.

(5) Miscellaneous effects

Local anesthesia: test of J. Regnier—Doctoral Dissertation, Med., 203 pages, Bruilliard St Dizier 1929.

A 1% solution shows local anesthetic properties superior to Lidocaine.

Diuretic effect (W. LIPSCHITZ J. Pharmacol. Exp. Ther., 79, 97, 1943) in rats.

The compound of 3-tertiobutylamino-1-[(1,4-benzodioxan)-2-yl-methoxy]-2-propanol maleate does not have any diuretic power.
Dose: 100 mg/kg orally.
Urinary excretion with compound of 3-tertiobutylamino-1-[(1,4-benzodioxan)-2-yl-methoxy]-2-propanol maleate: 35%
Control: 28%

(C) Therapeutic Applications

In view of their pharmacological properties and their low toxicity, these compounds and more particularly the compound 3-tertiobutylamino-1-[(1,4-benzodioxan)-2-yl-methoxy]-2-propanol maleate can be used in therapy for the treatment of cardiac disturbances and more particularly hypertension.

These compounds can be used in the form of pharmaceutical compositions in which the active compound is mixed with pharmaceutically acceptable non-toxic diluent vehicles which facilitate their bioavailability.

These compounds can be administered parenterally, intravenously or by mouth or rectal route. The doses of administration may vary in rather large proportions as a function of the method of administration selected as well as the type and seriousness of the ailment to be treated.

The compounds may, for instance, be in the form of tablets, capsules, suppositories, aqueous or oil solutions, aqueous or oil suspensions, emulsions, dispersible powders or solutions in injectable oil or aqueous suspensions.

We claim:

1. A method of preparing a compound of the formula

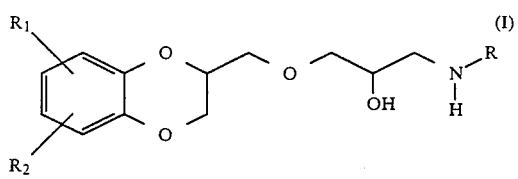

in which
$R_1$ and $R_2$ may be identical or different and represent a hydrogen or halogen atom or a lower alkyl, lower alkoxy, nitro or acetyl group, and
R represents a lower alkyl or lower aralkyl group, or a salt thereof with a therapeutically-acceptable inorganic or organic acid, characterized by the step of reacting a glycidyl ether of formula III

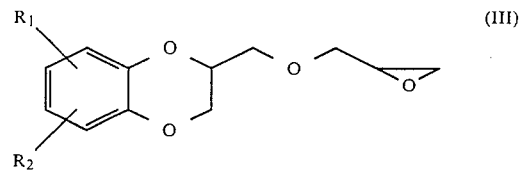

with a primary amine of formula IV $R-NH_2$ in a solvent for the reaction, for a period of time and at a temperature sufficient to produce the desired compound of formula I, and also characterized by the additional step of first producing the glycidyl ether of formula III by reaction of a 2-hydroxymethyl-1,4-benzodioxan of formula II

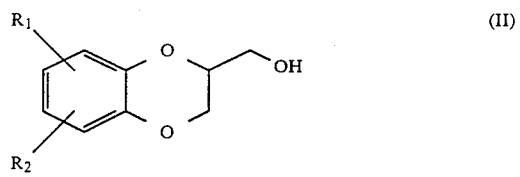

in which $R_1$ and $R_2$ have the same meanings as those given in the foregoing, with epichlorohydrin in the presence of a base and in the presence of a catalyst of the quarternary ammonium type.

2. A method according to claim 1, characterized by the fact that the primary amine IV is isopropylamine or tertiobutylamine.

3. A method according to claim 1, characterized by the fact that the catalyst of quaternary ammonium type is tetrabutylammonium hydrogen sulfate.

4. A method according to claim 1, characterized by the fact that the base is 50% aqueous caustic soda.

5. The method of claim 1, wherein the solvent is an alcohol.

6. The method of claim 5, wherein the alcohol is methanol.

7. The method of claim 1, wherein the substituents $R_1$ and $R_2$ are selected from the group consisting of hydrogen, halogen, lower-alkyl, lower-alkoxy, nitro, and acetyl.

8. The method of claim 1, wherein the substituents $R_1$ and $R_2$ are selected from the group consisting of hydrogen, 6-methyl, 5-methyl, 7-methyl, 8-methyl, 5-chloro, 7-chloro, 7-nitro, 7-methoxy, 6-acetyl, 5,7-dimethyl, and 6,7-dichloro.

9. The method of claim 7 wherein R is a branched-chain lower-alkyl group.

10. The method of claim 9, wherein R is a tertiobutyl radical and wherein both $R_1$ and $R_2$ are hydrogen, and wherein the end product is isolated as an acid addition salt.

11. The method of claim 10, wherein the end product is isolated as the maleate.

* * * * *

UNITED STATES PATENT AND TRADEMARK OFFICE
CERTIFICATE OF CORRECTION

PATENT NO. : 4,539,413

DATED : September 3, 1985

INVENTOR(S) : Gilbert Mouzin, Henri Cousse and Pol Vilain

It is certified that error appears in the above-identified patent and that said Letters Patent is hereby corrected as shown below:

Col. 1, lines 33 & 34; "therapeutically acceptable" should read -- therapeutically-acceptable --

Col. 1, lines 35 & 36; "therapeutically acceptable" should read -- therapeutically-acceptable --

Col. 7, line 58; insert -- benzodioxan)-2-yl-methoxy]-2-propanol -- at the end of the line Signed and Sealed this Twenty-first Day of January 1986

[SEAL]

Attest:

DONALD J. QUIGG

Attesting Officer

Commissioner of Patents and Trademarks